United States Patent [19]
Häseler
[11] 4,376,216
[45] Mar. 8, 1983

[54] PROCESS FOR THE PURIFICATION OF PHOTOGRAPHIC DEVELOPER SUBSTANCES

[75] Inventor: Helmut Häseler, Leverkusen, Fed. Rep. of Germany

[73] Assignee: Agfa-Gevaert AG, Leverkusen, Fed. Rep. of Germany

[21] Appl. No.: 289,415

[22] Filed: Aug. 3, 1981

[30] Foreign Application Priority Data

Aug. 12, 1980 [DE] Fed. Rep. of Germany ....... 3030480

[51] Int. Cl.$^3$ ............................................ C07C 85/26
[52] U.S. Cl. .................................... 564/438; 564/437
[58] Field of Search ............................... 564/437, 438

[56] References Cited

U.S. PATENT DOCUMENTS 2,019,032 10/1935 Weiss et al. .................... 564/437 X
2,035,510 3/1936 Semenoff ........................... 564/438
2,744,938 5/1956 Urban ............................ 564/437 X
2,950,319 8/1960 Schenck et al. .................... 564/437
3,184,511 5/1965 Bevan et al. ........................ 564/437
3,203,994 8/1965 Spiegler .............................. 564/437
3,301,903 1/1967 Cryer et al. ......................... 564/437

FOREIGN PATENT DOCUMENTS 697087 11/1964 Canada ................................ 564/437
53-77024 7/1978 Japan .................................. 564/438
858850 1/1961 United Kingdom ................ 564/437

*Primary Examiner*—John Doll
*Attorney, Agent, or Firm*—Connolly and Hutz

[57] ABSTRACT

A new process for the purification of photographic developer compounds using an anionic surfactant wherein unwanted impurities are removed either by being precipitated or dissolved.

In this process the developer substance is freed from difficult to remove impurities.

8 Claims, No Drawings

PROCESS FOR THE PURIFICATION OF PHOTOGRAPHIC DEVELOPER SUBSTANCES

This invention relates to a process for the purification of organic substances. Organic compounds which are required in a high degree of purity frequently contain troublesome impurities. These may be introduced in the course of production of the product, for example, or be produced by partial decomposition, e.g. oxidation, of the originally pure compound.

Many p-phenylene diamine compounds, for example, tend to form oxidation products which are difficultly soluble in aqueous solutions, particularly in an alkaline medium. These compounds include in particular those p-phenylene diamine compounds which are used as colour developer substances for the colour development of photographic materials containing silver halide. They tend to form difficultly soluble, brown developer oxidation products in the course of the preparation or storage thereof, particularly in the absence of anti-oxidants. These impurities render the developer solution cloudy, particularly the more highly concentrated replenishing developer solutions, and thereby impair photographic processing. If the developer solutions contain benzyl alcohol to improve the development properties, the benzyl alcohol is very liable to form into droplets which are more highly soluble than the remainder of the solution and therefore contain the impurities. When this happens, a very troublesome tar is formed.

It is an object of the present invention to provide a process for the purification of organic compounds to remove undesirable impurities. In particular, the present invention is based on the object of providing a process by which p-phenylenediamine compounds could be freed from oxidation products which are difficult to dissolve in aqueous solutions.

A process for the purification of organic compounds to remove organic impurities has now been found in which the organic compound is treated with a surfactant. The organic impurities in question are more particularly impurities which are difficultly soluble in aqueous solutions, in particular in an alkaline medium. By "surfactants" are meant surface active substances. Information on this subject may be found in the article by Joseph Hansmann in the Journal "Adhäsion", 1978, page 246 et seq.

In the process according to the present invention, the treatment with the surfactant is generally carried out in the aqueous phase at a pH at which the surfactant precipitates.

The process according to the present invention is particularly suitable for the purification of organic compounds of the p-phenylene diamine type. These compounds are preferably purified using anionic surfactants. Suitable anionic surfactants have been indicated, for example, in the above-mentioned article from the Journal "Adhäsion", on page 246, Table 2. Particularly preferred surfactants contain a $—COO^-$, $—OSO_3^-$ or $—SO_3^-$ group.

When anionic surfactants are used, the pH is generally below 4.5, preferably below 3, in particular below 1.

The process according to the present invention is particularly suitable for the purification of p-phenylene diamine compounds of the type suitable for use as photographic colour developer substances for the development of photographic materials containing silver halide. Particularly suitable compounds of this type are those corresponding the the following general formula (I):

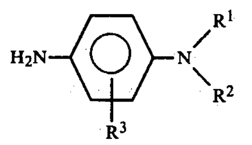

(I)

wherein $R^1$ and $R^2$, which may be the same or different, represent one of the conventional substituents used for developer substances, in particular an alkyl group having from 1 to 4 carbon atoms; and $R^3$ represents hydrogen or one of the conventional substituents for photographic developer substances, in particular an alkyl group having from 1 to 4 carbon atoms.

The substituents $R^1$, $R^2$ and $R^3$ may in turn be substituted with substituents, such as OH, O-alkyl, $SO_3H$ or $—NH—SO_2—CH_3$.

Developer substances of this type are exemplified below:

4-amino-N,N-diethyl-aniline, N,N-dimethyl-p phenylene diamine, 4-amino-3-methyl-N-ethyl-N-methoxyethylaniline, 2-amino-5-diethylaminotoluene, N-butyl-N-ω-sulphobutyl-p-phenylene diamine, 2-amino-5-(N-ethyl-N-β-methanesulphonamidothyl-amino)-toluene, N-ethyl-N-β-hydroxyethyl-p-phenylene diamine, N,N-bis-(β-hydroxyethyl)-p-phenylene diamine and 2-amino-5-(N-ethyl-N-β-hydroxyethylamino)-toluene. Other suitable colour developers have been described, for example, in J.Amer.Chem.Soc. 73, 3100 (1951).

According to the present invention, a solution of the organic compound to be purified may first be prepared, preferably an acid solution. It may be adjusted to a suitable pH by the addition of acids in known manner. The surfactant is then added, optionally in the form of a solution, and the components are mixed. The unwanted impurities are either deposited on the slowly precipitating surfactant or dissolved in so that they may be removed in known manner. If the substance to be purified is a colour developer substance, the purified filtrate is directly ready for use for the preparation of a photographic developer or of a partial concentrate.

The quantity of surfactant to be used depends on the degree of contamination of the substance to be purified and on the form in which the surfactant precipitates.

The surfactant, in the form of an aqueous or alcoholic solution, is generally used in a quantity of from 1 to 10 g per mol of substance to be purified, although quantities above or below this range may be optimal. The process of purification may be repeated if necessary.

The process according to the present invention may, alternatively, be carried out by adding the substance to be purified, in particular an aqueous acid solution of a p-phenylene diamine, to the solid wetting agent. In that case, the wetting agent may be contained in a column and the substance to be purified is then introduced into the column from the top to be discharged from the bottom of the column as purified substance. The wetting agents given in the following Table I are particularly preferred. These compounds may be used as aqueous or alcoholic or aqueous-alcoholic solutions.

TABLE I

| Surfactant No. | Compound |
|---|---|
| 1 | $F_{17}C_8SO_3^-.N^+(C_2H_5)_4$ |
| 2 | 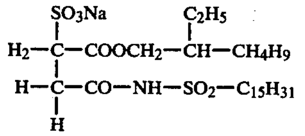 |
| 3 | 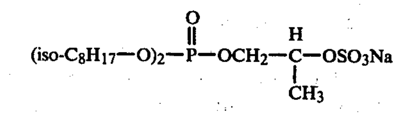 |
| 4 | Penta-decenyl-succinic acid diglycolide sodium salt |
| 5 | Perfluoro-caprylic acid-$NH_4$—salt |
| 6 | 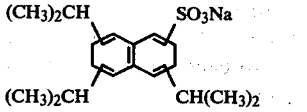 |
| 7 | 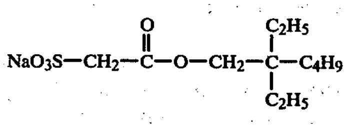 |
| 8 | 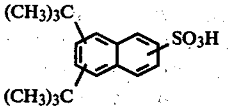 |
| 9 | 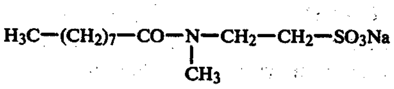 |
| 10 | 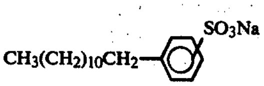 |
| 11 | Glycerol-1,3-bis-(2-ethyl-hexyl-ether)-2-sulphuric acid ester, Na salt |

The purification of some organic compounds is exemplified in the following Examples.

EXAMPLE 1

Purification of compound A corresponding to the formula:

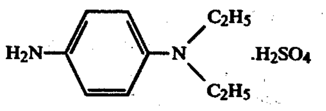

(A)

120 g of a contaminated compound A are dissolved in 300 ml of water. 30 ml of a 96% sulphuric acid are then added to adjust the pH to 0.5. 25 ml of a 4% solution of surfactant No. 10 are then added and the mixture is stirred and then left for 3 hours without stirring. The impurities settle during this time and may be removed by filtration. A clear solution of compound A is obtained. This solution may immediately be used for the preparation of developer concentrates.

Separation of the unwanted impurities may be controlled quantitatively by colorimetric comparison of the solution of compound A before and after precipitation of the surfactant. This is carried out by measuring the samples in a colorimeter at a wavelength of 550 nm. The samples should be adjusted to the range of measurement by uniform dilution according to the density of the colour.

Compound A may also be purified using other surfactants in analogous manner. The effects of purification using these surfactants may be seen from Table 2 which contains the results of the colorimeter measurements described above.

TABLE 2

| Surfactant | Extinction |
|---|---|
| Solution before treatment using surfactant | 0.70 |
| Filtrate after precipitation using surfactant No. 1 | 0.03 |
| Filtrate after precipitation using surfactant No. 2 | 0.09 |
| Filtrate after precipitation using surfactant No. 3 | 0.15 |
| Filtrate after precipitation using surfactant No. 5 | 0.01 |
| Filtrate after precipitation using surfactant No. 6 | 0.03 |
| Filtrate after precipitation using surfactant No. 7 | 0.12 |
| Filtrate after precipitation using surfactant No. 8 | 0.03 |
| Filtrate after precipitation using surfactant No. 10 | 0.05 |
| Filtrate after precipitation using surfactant No. 11 | 0.13 |

EXAMPLE 2

Purification of Compound B corresponding to the following formula:

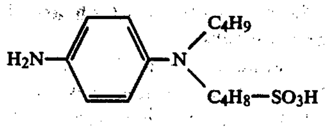

(B)

150 g of the contaminated compound B are dissolved in 300 ml of water. A pH of 0.4 results after the addition of 40 ml of 96% sulphuric acid. 90 ml of a 4% solution of surfactant No. 6 are then added and the mixture is stirred. When the mixture has been left to stand for 3 hours without stirring, the impurities have settled and may be removed by filtration. Compound B is purified in a similar manner using the surfactants listed in Table 3. Extinction of the samples is determined as in Example 1 and the results are indicated in Table 3.

TABLE 3

| Surfactant | Extinction |
|---|---|
| Solution before treatment using surfactant | 1.0 |
| Filtrate after precipitation using surfactant No. 1 | 0.65 |
| Filtrate after precipitation using surfactant No. 2 | 0.51 |
| Filtrate after precipitation using surfactant No. 3 | 0.80 |
| Filtrate after precipitation using surfactant No. 6 | 0.78 |
| Filtrate after precipitation using surfactant No. 9 | 0.82 |

EXAMPLE 3

Purification of compound C corresponding to the formula:

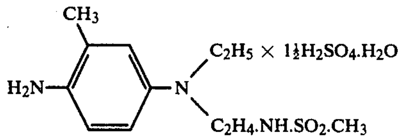

(C)

180 g of the contaminated compound C are dissolved in 300 ml of water. The solution is at a pH of 0.5. To this solution are added 18 ml of a 4% solution of surfactant No. 1, and the mixture is stirred and then left to stand for 3 hours without stirring. The precipitate which forms during this time is removed by filtration. Compound C is purified in a similar manner, using the surfactants indicated in Table 4. Table 4 also shows the extinctions of the samples examined as in Example 1.

TABLE 4

| Surfactant | Extinction |
|---|---|
| Solution before treatment using surfactant | 0.50 |
| Filtrate after precipitation using surfactant No. 1 | 0.24 |
| Filtrate after precipitation using surfactant No. 2 | 0.30 |
| Filtrate after precipitation using surfactant No. 6 | 0.28 |
| Filtrate after precipitation using surfactant No. 7 | 0.39 |
| Filtrate after precipitation using surfactant No. 11 | 0.26 |

Examples 1 to 3 show that aqueous solutions of the substances A, B and C may be purified in accordance with the present invention. This is demonstrated by the markedly reduced extinction.

EXAMPLE 4

This Example demonstrates that the compounds which have been purified according to the present invention may advantageously be used for the preparation of colour developer solutions or colour developer replenishing solutions.

A replenishing developer solution I is first prepared in known manner, using compound C of Example 3 as colour developer substance. A developer partial concentrate of compound C is first prepared from 180 g of compound C, 300 ml of water and 35 ml of a 30% sodium disulphite solution. The resulting solution is then made up to 600 ml with water. This solution is known as the partial concentrate.

The replenishing developer solution I has the following composition:

800 ml of water
22 ml of developer partial concentrate (without addition of surfactant solution)
14 ml of diethylene glycol
18 ml of benzyl alcohol (benzaldehyde content <0.05%)
4g of hydroxylamine sulphate
2 g of potassium disulphite
1 g of diethylene triaminopentacetic acid
3 g of sodium hydroxide
100 ml of potassium carbonate solution (330 g/l) made up with water to 1 liter.

The solution also contains 1 g of a white toner.

A replenishing developer solution II is prepared in a similar manner, but instead of the partial concentrate indicated above there is used a partial concentrate in which the colour developer substance has been purified according to Example 3.

On visual examination, the developer regenerator solution I is found to be distinctly more cloudy than replenishing developer solution II. The following light absorption values are measured in a colorimeter at a wavelength of 500 nm and a layer thickness of 10 mm:

| | |
|---|---|
| Developer replenishing solution I: | 17% |
| Developer replenishing solution II: | 6% |

Developer replenishing solution II containing a colour developer substance which has been purified according to the present invention thus has a substantially lower absorption.

The developer replenishing solution indicated in Example 4 is ready for use as a developer bath after the addition of water and starting substances.

I claim:

1. A process for the purification of a compound of the p-phenylene diamine series to free it from organic impurities, wherein said compound is treated in an aqueous solution with an anionic surfactant of a pH at which the the surfactant precipitates.

2. Process according to claim 1, wherein the surfactant contains a —COO⁻, $OSO_3^-$ or $-SO_3^-$ group.

3. Process according to claim 2, wherein the surfactant corresponds to the following formula $$F_{17}C_8SO_3^-.N^+(C_2H_5)_4.$$

4. Process according to claim 1, wherein the pH is below 4.5.

5. Process according to claim 4, wherein the pH is below 3.0.

6. Process according to claim 1, wherein the p-phenylene diamine is a photographic colour developer substance.

7. Process according to claim 6, wherein the p-phenylene diamine corresponds to the folowing general formula

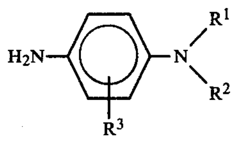

(I)

wherein $R^1$ and $R^2$, which may be the same or different, represent one of the conventional substituents for photographic developer substances; and $R^3$ represents hydrogen or one of the conventional substituents for photographic developer substances.

8. Process according to claim 7, characterised in that $R^1$, $R^2$ and $R^3$ in general formula (I) have the following meanings:

$R^1$ and $R^2$ represents substituted or unsubstituted alkyl groups having from 1 to 4 carbon atoms; and $R^3$ represents hydrogen or a substituted or unsubstituted alkyl group having from 1 to 4 carbon atoms.

* * * * *